United States Patent
Zahnd et al.

(10) Patent No.: US 10,549,326 B2
(45) Date of Patent: Feb. 4, 2020

(54) SWIVEL FOR SEWER CLEANING SYSTEM

(71) Applicant: iPEK INTERNATIONAL GmbH, Sulzberg (DE)

(72) Inventors: Fabian Zahnd, Kempten (DE); Peter Henn, Krugzell (DE)

(73) Assignee: iPEK INTERNATIONAL GMBH, Sulzberg (DE)

( * ) Notice: Subject to any disclaimer, the term of this patent is extended or adjusted under 35 U.S.C. 154(b) by 234 days.

(21) Appl. No.: 15/146,033

(22) Filed: May 4, 2016

(65) Prior Publication Data
US 2016/0325321 A1 Nov. 10, 2016

(30) Foreign Application Priority Data

May 6, 2015 (DE) .................... 20 2015 102 328 U

(51) Int. Cl.
| | |
|---|---|
| *B08B 9/049* | (2006.01) |
| *E03F 9/00* | (2006.01) |
| *B08B 9/04* | (2006.01) |

(52) U.S. Cl.
CPC .............. *B08B 9/0495* (2013.01); *B08B 9/04* (2013.01); *E03F 9/00* (2013.01)

(58) Field of Classification Search
CPC ....... B08B 9/0495; B08B 9/051; B08B 9/053; E03F 9/00
See application file for complete search history.

(56) References Cited

U.S. PATENT DOCUMENTS 4,107,738 A * 8/1978 Van Norman ............ E03F 7/00
348/84
4,756,324 A * 7/1988 Larsson ................ B08B 9/0495
134/167 C
(Continued)

FOREIGN PATENT DOCUMENTS

CN 204066206 U * 12/2014
DE 9310192 U * 8/1993
(Continued)

OTHER PUBLICATIONS

Machine translation of DE10255221A1, dated Nov. 2002. (Year: 2002).*
(Continued)

*Primary Examiner* — Joseph L. Perrin
*Assistant Examiner* — Kevin G Lee
(74) *Attorney, Agent, or Firm* — Myers Wolin, LLC

(57) ABSTRACT

Provided is a rinsing head for a pipe or sewer inspection system, comprising imaging means arranged at the front end and rinsing means arranged axially behind the imaging means. The rinsing means comprises a number of rinsing nozzles with openings arranged on its lateral surface and spaced apart from each other circumferentially. The rinsing nozzles are connected via to an inlet opening for pressurized water provided at the rear end of the rinsing means. A WLAN module is arranged within the rinsing head and coupled to a camera module of the imaging means operatively. An antenna unit of the WLAN module is arranged axially behind the rinsing nozzles with at least one antenna arranged at least partially radially around the inlet opening for pressurized water. The WLAN module and the antenna unit are adapted to transmit image and/or video data provided by the camera module to a control/display means.

12 Claims, 3 Drawing Sheets

(56) References Cited

U.S. PATENT DOCUMENTS

| | | | | |
|---|---|---|---|---|
| 2014/0072012 A1* | 3/2014 | Kreutzer | ............ | G01J 5/04 |
| | | | | 374/121 |
| 2014/0073238 A1* | 3/2014 | Henn | ............ | G06T 1/0007 |
| | | | | 455/7 |
| 2015/0077537 A1* | 3/2015 | Thursby | ............ | E21B 47/0002 |
| | | | | 348/85 |
| 2015/0331136 A1* | 11/2015 | Tinlin | ............ | B08B 9/0495 |
| | | | | 134/18 |

FOREIGN PATENT DOCUMENTS

| | | | | |
|---|---|---|---|---|
| DE | 102 55 221 A1 | 6/2004 | | |
| DE | 10255221 A1 * | 6/2004 | ............ | B08B 9/0495 |
| WO | WO-03025488 A1 * | 3/2003 | ............ | C03B 5/24 |

OTHER PUBLICATIONS

Examination report with written opinion for corresponding German Patent Application No. 10 2015 107 098.7 dated Jan. 18, 2016 with an English translation, URL: <https://translate.googleusercontent.com/translate_f>.

European Communication issued for corresponding European Patent Application No. 16168025.1 dated Jul. 20, 2018 with a machine generated English translation.

\* cited by examiner

SWIVEL FOR SEWER CLEANING SYSTEM

CROSS REFERENCE TO RELATED APPLICATIONS

This application claims priority to German Application 20 2015 102 328.6, filed May 6, 2015, the contents of which are incorporated by reference herein.

TECHNICAL FIELD

The invention relates to a rinsing head for a sewer and pipe inspection system, wherein the rinsing head comprises an imaging means and a rinsing means having a number of nozzles and an inlet opening for pressurized water.

BACKGROUND

In the field of sewer inspection and/or sewer cleaning it is known to use sewer inspection systems or pipe cleaning systems which may be inserted into the sewer to be inspected or cleaned, and which may be advanced within the sewer. For example, for cleaning sewers it is known to use rinsing heads to which a high pressure rinsing hose may be connected. The water discharge from rinsing nozzles directed backwards effects an advancing of the rinsing head within the sewer. Upon pulling the rinsing head out of the sewer, the water discharge effects cleaning of the sewer.

Further, it is known to arrange at the rinsing head, an imaging means by means of which the interior of the sewer may be inspected optically during a rinsing process. The image data of the imaging means has to be transmitted during the rinsing process to a display means outside of the sewer. For this, it is known to connect the rinsing head or the imaging means of the rinsing head via a cable connection to the display means.

However, with respect to the data transmission via cable connections, it is disadvantageous that the cable connections are subject to high wear due to the use in a harsh environment during sewer inspections or sewer cleaning, and may be damaged easily, requiring a partial or complete replacement of the cable connections. Therefore, it is necessary to provide the cables or cable connections with a stable and substantially wear-resistant sheath, however, involving a high additional weight and high additional costs of the cables.

A further substantial disadvantage is that the cable has to be unwound from a cable drum or would onto it during a cable cleaning. The unwinding or winding of the cable, in particular, is problematic, if the cable has to be inserted into a sewer pipe simultaneously with a high pressure hose. This, on the one hand, leads to increased setup and operating times. On the other hand, the insertion of the cable into the sewer pipe together with the rinsing hose may adversely affect the wear of the cable. An attempt has been made to solve this problem by integrating the cable into the rinsing hose, for example, into the rinsing hose sheath. This, however, has the disadvantage that upon damage of the cable integrated into the rinsing hose, in the worst case, the entire rinsing hose has to be replaced.

During application of the sewer inspection system or sewer cleaning system in explosion-proof environments, moreover, it has to be ensured that the cables are not damaged or will not be damaged during the application.

SUMMARY

Therefore, the present invention is based on the object to at least partially avoid the disadvantages mentioned above, and to provide a rinsing head by means of which a reliable and simple inspection of a sewer during a cleaning procedure is ensured.

According to the invention, this object is solved by a rinsing head according to the independent claim. Preferred embodiments and configurations of the invention are specified in the respective dependent claims.

Accordingly, a rinsing head for a sewer or pipe inspection system is provided, comprising an imaging means arranged at the front end and a rinsing means arranged axially behind the imaging means, wherein the rinsing means comprises a number of rinsing nozzles, the water outlet openings of which are arranged on the lateral surface of the rinsing means spaced apart from each other in circumferential direction, wherein the rinsing nozzles are connected to an outlet opening for pressurized water provided at the rear end of the rinsing means via at least one water channel, a WLAN module is arranged in the rinsing head being coupled to the camera module of the imaging means operatively, an antenna unit of the WLAN module is arranged axially behind the rinsing nozzles, wherein the at least one antenna is arranged at least partially radially around the inlet opening for pressurized water, and the WLAN module and the antenna unit are adapted to transmit the image and/or video data provided from the camera module wirelessly to a control/display means.

Because the antenna unit is arranged axially behind the rinsing nozzles, the influence of the rinsing water being discharged from the rinsing nozzles on the transmission quality of the WLAN connection is reduced substantially. The transmission power, thus, can be kept correspondingly low.

The at least one antenna may be arranged at the rear side of the rinsing means.

The WLAN module may be arranged axially behind the rinsing nozzles or within the imaging means.

A cable channel may be formed within the wall of the rinsing means which extends from the rear side of the rinsing means in axial direction through the rinsing means, wherein an electrically conducting cable is arranged within the cable channel, by means of which the at least one antenna is coupled to the WLAN module, or the WLAN module is coupled to the camera module.

The rinsing means may be configured as monolithic body, in which the rinsing nozzles are arranged, and in which at least one water channel, the outlet opening for pressurized water, and the cable channel are formed.

At the rear side of the rinsing means, a cover may be provided for covering the antenna unit.

The cover may comprise plastic and/or may be arranged releasably at the rear side of the rinsing means.

The imaging means may comprise a housing, in the interior of which an accommodation space for accommodating the camera module is provided.

Preferably, the housing is arranged at the rinsing means releasably. At the front end, the housing may comprise an opening arranged coaxially with respect to the optical axis of the camera module.

A double glazing pane may be arranged in the opening, the glass panes of which are arranged spaced apart from each other, wherein both glass panes form a substantially pressure-tight cavity. The double glazing pane closes the opening.

The housing may be formed with double walls, wherein both walls of the housing form a substantially pressure-tight cavity.

Alternatively or additionally, a sleeve may be arranged within the housing surrounding the camera module and/or the WLAN module, wherein a substantially pressure-tight cavity is formed between the housing and the sleeve.

Preferably, the cavity between the two glass panes and the cavity between both walls of the housing, or the cavity between the housing and the sleeve are connected to each other.

An overpressure may be applied to the cavities, wherein a pressure sensor is assigned to at least one cavity.

An energy storage, in particular, an accumulator, may be arranged within the rinsing head for supplying electrical energy to the WLAN module and the camera module.

In the rinsing head, a secondary coil means of an inductive charging system may be arranged for inductive charging of the energy storage.

A storage means may be arranged within the rinsing head being operatively coupled to the camera module for storing of image and/or video data provided by the camera module.

A pressure sensor may be assigned to the water channel for monitoring the water pressure applied to the rinsing means, wherein the pressure data may be transmitted to the control/display means via the WLAN module.

The WLAN module may be adapted to receive control data from the control/display means, wherein the control data comprises at least data for controlling the camera module and/or data for controlling the rinsing nozzles.

The lateral surface of the rinsing means may have, for example, the shape of an hourglass, wherein the water outlet openings of the rinsing nozzles are arranged in the portion of the lateral surface directed rearwards.

Further, a sewer or pipe inspection system is provided comprising a control/display means and a rinsing head according to the invention, wherein the image and/or video data provided by the camera module of the rinsing head may be transmitted wirelessly via the WLAN module of the rinsing head to the control/display means.

BRIEF DESCRIPTION OF THE DRAWINGS

Further details and features of the invention as well as concrete embodiments of the invention can be derived from the following description in connection with the drawing, in which.

DETAILED DESCRIPTION

Figure 1A:
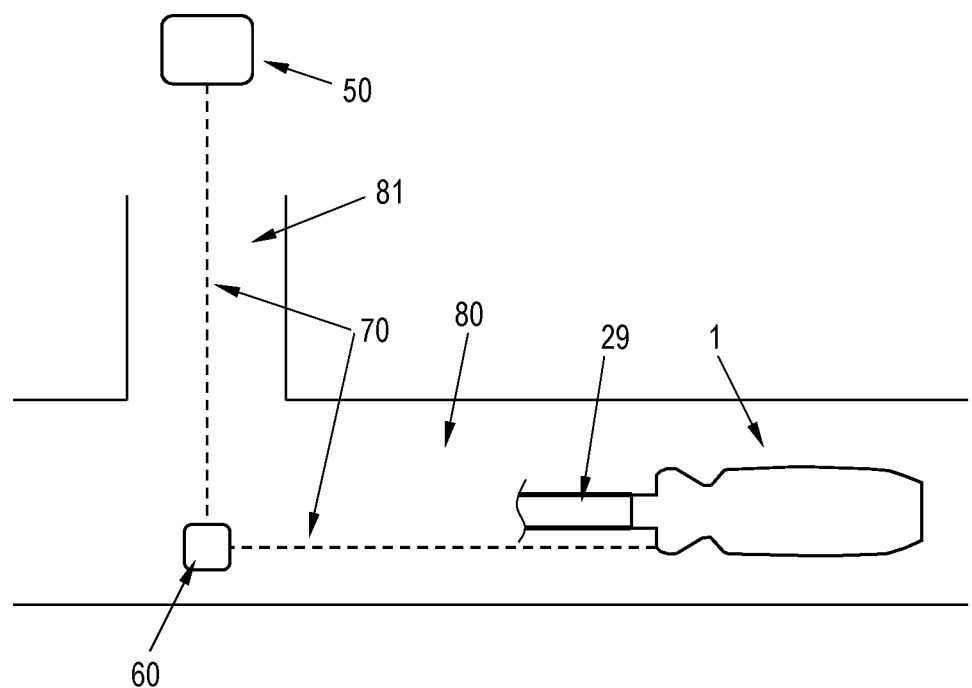
FIG. 1a shows a system according to the invention with a rinsing head according to the invention and a control/display means.

FIG. 1a shows a system according to the invention with a rinsing head 1 according to the invention and a control/display means 50.

The rinsing head 1 and the control/display means 50 respectively comprise a WLAN module, via which a WLAN connection 70 between the rinsing head 1 and the control/display means 50 may be established. Via the WLAN connection 70, image data (e.g., video data) of a camera module arranged at the rinsing head 1 is transmitted to the control/display means 50.

Preferably, the WLAN connection 70 is configured as bi-directional connection such that also control data can be transmitted from the control/display means 50 to the rinsing head 1. For example, the camera module (e.g., focal distance, illumination) or the rinsing nozzles (e.g., water outlet angle) of the rinsing head can be controlled.

Further, it may be advantageous, if the system according to the invention comprises a repeater 60. On the one hand, the operational range of the WLAN connection may be increased by the repeater 60. On the other hand, the WLAN signal may be "diverted" from the channel 80 to the duct 81 by means of the repeater 60. According to its intended application, the repeater 60 may be arranged at the bottom of the duct 81 or within the channel 80.

A high pressure rinsing hose 29 is connected to the rinsing head 1, via which the rinsing water is supplied to the rinsing head.

A sewer cleaning can be carried out by means of the inventive system, wherein the result of the cleaning may be monitored at the same time at the control/display means 50 without cable connections being required for the data transmission from the rinsing head 1 to the control/display means 50. By omission of the cable connections, moreover, the setup effort may be reduced substantially, because in the end, now, only the high pressure rinsing hose 29 with the rinsing head 1 attached thereto has to be inserted.

Figure 1B:
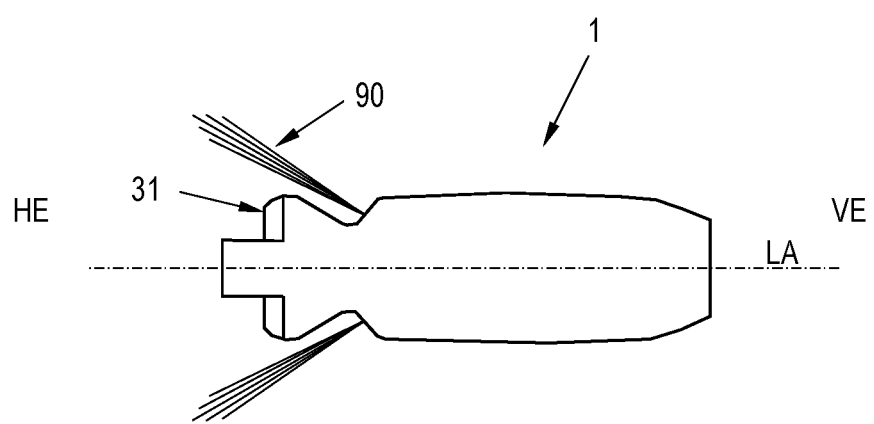
FIG. 1b shows a rinsing head with water jets being discharged according to the invention.

FIG. 1b shows a rinsing head 1 according to the invention schematically with water jets 90 being discharged from rinsing nozzles directed rearwards, wherein the antenna unit 31 of the WLAN module is located in the interior of the water cone being free of water.

Figure 2:
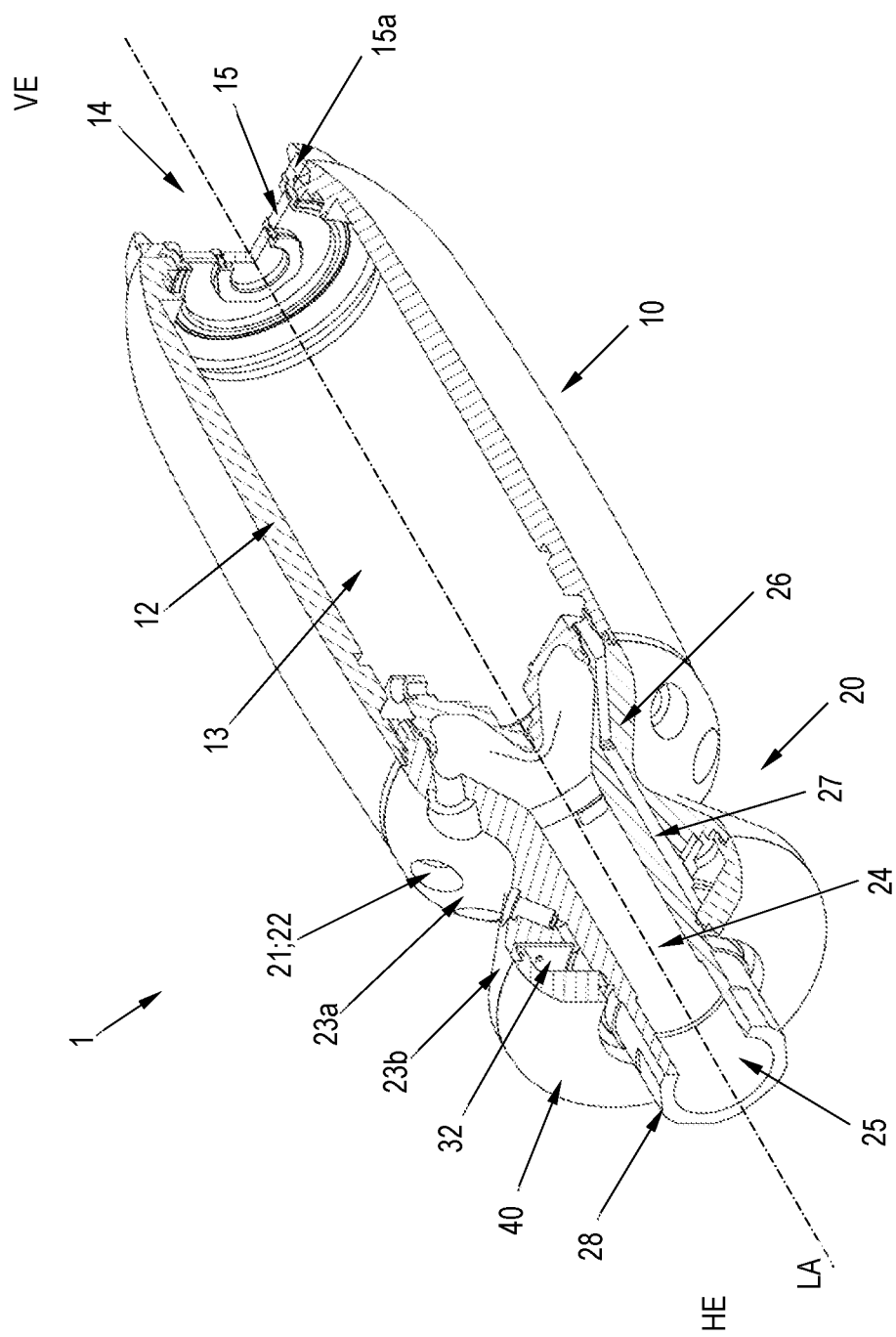
FIG. 2 shows a rinsing head according to the invention in perspective view.
Figure 3:
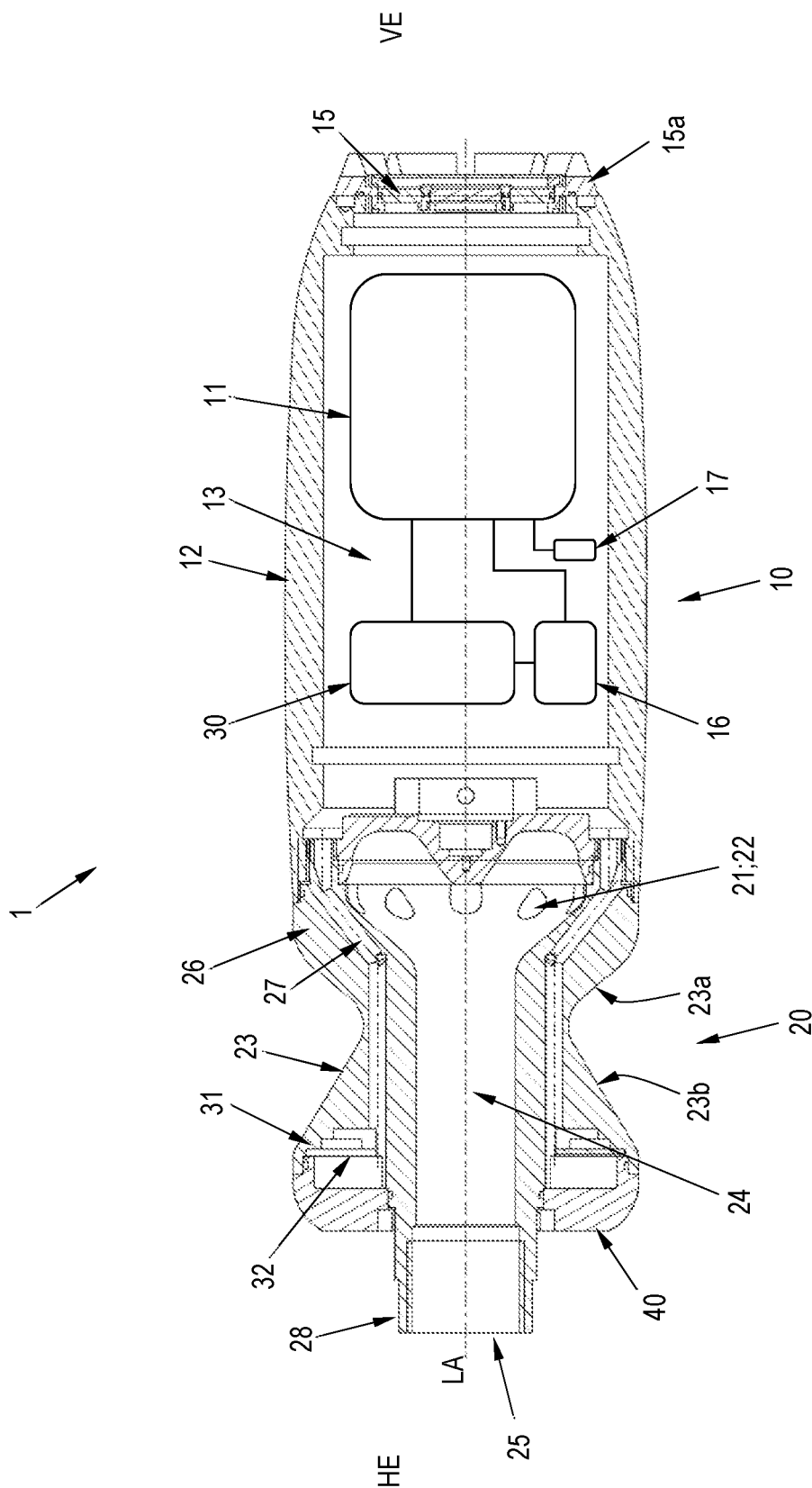
FIG. 3 shows a rinsing head according to the invention in longitudinal section.

FIG. 2 and FIG. 3 show a rinsing head 1 according to the invention in a perspective view (FIG. 2) and in a longitudinal section along the longitudinal axis LA (FIG. 3).

The rinsing head 1 basically consists of three parts: the imaging means 10, the rinsing means 20, and the antenna unit 31.

The imaging means 10 comprises a housing 10 which, in this embodiment, is formed substantially cylindrically and has a circular cross section. According to the invention, the housing 10 may also have another cross section, for example, a square or octagonal cross section. The housing 10 is made from a stable material, preferably metal, in particular, steel.

At the front end VE, the housing 10 has an opening 14, which is closed by a double glazing pane 15. The double glazing pane 15 is surrounded by a retaining ring 15a, which may be made from metal, or is held in a retaining ring. The double glazing pane 15 is fixed by means of the retaining ring 15a to the front end VE of the housing, for example, by means of a plug or threaded connection. The fixation of the double glazing pane 15 by means of the retaining ring 15a at the housing 10 is made such that the opening 14 is closed substantially or completely air- and fluid-tightly.

The double glazing pane 15 and the retaining ring 15a are configured such that between the two glass panes, a pressure-tight cavity is formed, to which an overpressure with respect to the ambient pressure may be applied.

The interior of the housing 12 forms an accommodation space 13 for accommodating a camera module 11, a WLAN module 30, an accumulator 16, and a storage means 17. By means of the accumulator 16, the camera module 11 and the WLAN module 30 are supplied with electrical energy.

The accumulator itself may be charged by means of inductive charging technique. For this, a secondary coil (not shown here) of an inductive charging system is arranged within the rinsing head.

The WLAN module 30 is connected to the camera module 11 operatively such that the image and/or video data provided by the camera module 11 may be transmitted to a control/display means 50 wirelessly. The WLAN module 30, moreover, is adapted to receive control data from the control/display means 50 wirelessly such that, for example, the camera module 11 may be controlled wirelessly via the control/display means 50 (e.g., adjusting the focal distance of the camera module, or controlling the illumination means of the camera module).

The storage means 17 is coupled to the camera module 11 operatively and may be configured, for example, as memory card. During an inspection or cleaning process, the image and/or video data provided by the camera module 11 may be stored in the storage means 17 completely. Thereby, even with difficult receiving situations, no image and/or video data is lost. According to an embodiment, the memory card may be withdrawn from the rinsing head. Alternatively, the memory card may also be read via the WLAN module 30.

According to an embodiment of the invention, the housing 12 may be configured double-walled. The two walls of the housing 12, thereby, form a substantially pressure-tight cavity, to which an overpressure with respect to the ambient pressure may be applied.

According to an alternative embodiment, a pressure- and fluid-tight sleeve may be arranged within the accommodation space 13, wherein the camera module 11, the WLAN module 30, and the other electronic components 16, 17 may be arranged within the sleeve. The cavity formed between the sleeve and the wall of the housing 12, is configured substantially pressure tightly such that an overpressure with respect to the ambient pressure may be applied to it.

The pressure-tight cavity formed between the two glass panes is connected to the pressure-tight cavity of the double-walled housing 12 or to the pressure-tight cavity formed by the sleeve and the housing. All and all, a pressurized capsule is provided thereby, in which the camera module 11, the WLAN module 30 and the other electronic components 16, 17 are arranged. A pressure sensor is assigned to the pressure-tight cavity thus formed, by means of which the pressure may be monitored within the cavity continuously. Upon pressure loss, for example, due to damage of the external glass pane of the double glazing pane 15, this can be signalized the user, who then may interrupt the cleaning procedure in order to avoid further damages of the rinsing head, in particular, however damages of the electronic components. Hereby, it is advantageous that, for example, upon damage of the external glass pane of the double glazing pane 15, only water or dirt enters into the cavity, while the camera module 11, the WLAN module 30 and the other electronic components 16, 17 are still protected. Only if both glass panes of the double glazing pane 15 are damaged, humidity or dirt might reach the electronic components 11, 30, 16, 17.

The housing 10 is fixed with its rear end to the rinsing means 20, for example, by means of a plug or threaded connection. The fixation of the housing 10 at the rinsing means 20 is made such that the rear opening (the opening facing the rinsing means 20) of the housing is almost or completely closed air and fluid tightly by the rinsing means 20.

The electronic components 11, 30, 16, 17 arranged within the accommodation space 13 are fixed to the front end of the rinsing means 20 (the end facing the housing 10) preferably releasably via fixation means. Thereby, the housing 10 may be taken off or released from the rinsing means 20 without the electronic components 11, 30, 16, 17. In case the electronic components 11, 30, 16, 17 are arranged within the sleeve, the housing 10 may also be taken off without the sleeve. A replacement of the housing 10, for example, due to a damaged glass pane, may be accomplished in a simple manner and at low costs.

The rinsing means 20 is arranged axially behind the housing 10. The rinsing means 20 is configured in one piece or monolithically from a stable material, for example, steel. The rinsing means 20 at the rear end HE has a inlet opening for pressurized water 25, to which a high pressure rinsing hose (not shown here) may be connected or coupled. The inlet opening for pressurized water 25 is followed by a water channel 24, which is formed within the rinsing means 20. The rinsing water supplied to the rinsing means 20 is supplied to the rinsing nozzles 21 via the water channel 24. The rinsing nozzles 21 are arranged in radial direction and spaced apart from each other at the rinsing means 20. The rinsing nozzles may be inserted releasably into openings provided for this, which are connected to the water channel 24, or may be fixed within these openings.

According to a preferred embodiment, the lateral surface 23 of the rinsing means 20 has the shape of an hourglass. That means that the rinsing means 20 is tapered from the rear end and from the front end in axial direction. The rinsing nozzles 21, thereby, are arranged in each section 23a of the lateral surface 23, which is directed rearwards. Due to the inclination of the section 23a relative to the longitudinal axis LA of the rinsing head 1, the rinsing nozzles 21 are directed backwards such that the water being discharged from the rinsing nozzles 21, on the one hand, effect an advancing of the rinsing nozzle 1 within the channel, and upon pulling the rinsing head out of the channel, on the other hand, a cleaning of the channel.

Due to the section 23b of the lateral surface 23 opposing the section 23a also being inclined, the rear end of the rinsing head 1 is protected efficiently from water jets being discharged partially with several 100 bar from the rinsing nozzles.

The protection of the rear end of the rinsing head 1 (the end at which the inlet opening for pressurized water 25 is located) is particularly advantageous because at this rear end the antenna unit 31 of the WLAN module 30 is arranged. In operation, the antenna unit 31 of the WLAN module 30 is located in the interior of the water cone 90 free of water, as shown in FIG. 1b. Thereby, the influence of the rinsing water being discharged to the transmission quality of the WLAN connection is reduced substantially such that the transmission power may be kept correspondingly low.

Advantageously, a pressure sensor is assigned to the water channel 24, which preferably is coupled to the WLAN module. By means of this pressure sensor, the water pressure being actually applied to the rinsing head may be detected continuously, and may be transmitted to the control/display means 50 via the WLAN module 30. Thereby, the user is enabled to adapt the water pressure, as needed. Further, the water pressure may be recorded for documentation purposes together with the video signal, for example, on the integrated storage means 17. Further, for example, the water consumption and the cleaning may be adapted to the contamination degree and to the sewer condition. Damages at the sewer due to a water pressure being too high, thereby, can be avoided.

In the rinsing means 20, that means in the wall 26 of the rinsing means 20, a cable channel 27 is provided, which extends from the rear end to the front end of the rinsing means 20. The cable channel 27, thereby, extends completely within the wall 26 of the rinsing means 20 such that it is separated from the water channel 24 completely. At the front end of the rinsing means 20, the cable channel 27 leads into the accommodation space 13 of the housing 12. That means that, for example, upon damage of the external glass pane of the double glazing pane 15, no water or dirt may reach the cable channel 27. Electrically conducting cables for connecting the WLAN module 30 to the antenna unit 31 are provided in the cable channel 27.

According to an alternative embodiment of the rinsing head 1 according to the invention, the WLAN module 30 may also be arranged at the rear end of the rinsing means 20. In this case, an electrically conducting cable for connecting the WLAN module 30 to the camera module 11 is run in the cable channel 27.

An antenna unit 31 of the WLAN module 30 is arranged at the rear side or at the rear end of the rinsing means 20 with respect to the embodiment shown in FIG. 2 and FIG. 3. The antenna 32 of the antenna unit 31 is arranged radially around the opening for pressurized water 25. Instead of a single antenna, also several antennas may be provided, which are arranged spaced apart from each other and also radially around the opening for pressurized water 25. The arrangement of the antennas 32 at the rear end of the rinsing means 20 yields several advantages:

- except for the port 28 for the high pressure rinsing hose, nearly the entire area of the rear end of the rinsing means 20 may be used as effective antenna area. Partial covers, for example due to dirt, of the antenna/antennas, thereby, affects the transmission quality of the WLAN connection only minimally;
- the antenna/antennas are directed backwards without components of the rinsing head covering the antenna/antennas;
- the antenna/antennas are located within the interior of the water-free water cone of the rinsing water being ejected from the rinsing nozzles—thereby, the influence of the rinsing water being discharged on the transmission quality of the WLAN is substantially reduced; tests have revealed that the transmission power may be substantially reduced during the rinsing process compared to an antenna unit being arranged behind the rinsing nozzles and having the same effective antenna area, without an interruption of the WLAN connection occurring.

The antenna unit 31 is protected from water and dirt by means of a cover 40, which consists of a stable and preferably wear resistant plastic material. The cover 40 may be fixed to the rinsing means 20 releasably by means of a plug or threaded connection. Thereby, the cover may be replaced, if needed.

Moreover, a secondary coil of an inductive charging system may be arranged in the area of the antenna unit 31 in order to charge the accumulator 16.

The rinsing head 1 according to the invention advantageously enables an efficient wireless transmission of high resolution video data to the control/display means 50 in real time. Thereby, a cleaning procedure may be monitored continuously and in real time. Additional power/data cables do not need to be carried on. Moreover, the electronic components, for example, the camera module 11, being arranged in the rinsing head may be controlled via the WLAN connection by the control/display means 50. Besides the video data, also other sensor data may be transmitted from the rinsing head to the control/display means 50. By the rear-sided arrangement of the antenna unit 31 or the antennas 32, an efficient WLAN transmission is ensured also at low transmission power. By omission of additional power/data cables, setup times may be reduced substantially, enabling an efficient cleaning of sewers systems.

REFERENCE NUMERALS 1 rinsing head
10 imaging means
11 camera module of the imaging means 10
12 housing of the imaging means 10
13 accommodation space within the housing 12
14 opening at the front end of the housing 12
15 double glazing pane
15a metal ring
16 accumulator
17 storage means
20 rinsing means
21 rinsing nozzles
22 water outlet openings of the rinsing nozzles 21
23 lateral surface of the rinsing means 20
23a portion of the lateral surface 23 directed backwards
23b portion of the lateral surface 23 directed forwards
24 water channel
25 inlet opening for pressurized water
26 wall of the rinsing means 20
27 cable channel within the wall 26 of the rinsing means 20
28 port for the high pressure rinsing hose 29
29 high pressure rinsing hose
30 WLAN module
31 antenna unit of the WLAN module 30
32 antenna of the antenna unit 31
40 cover of the antenna unit 31
50 control/display means
60 repeater
70 WLAN connection
80 channel
81 duct
90 water jets
HE rear end of the rinsing head 1
VE front end of the rinsing head 1

What is claimed is:

1. A rinsing head (1) for a pipe or sewer inspection system, comprising an imaging means (10) arranged at the front end and a rinsing means (20) arranged axially behind the imaging means (10), wherein the rinsing means (20) comprises a number of rinsing nozzles (21), the water outlet openings (22) of which being arranged on the lateral surface (23) of the rinsing means (20) spaced apart from each other in circumferential direction, wherein the rinsing nozzles (21) are connected via at least one water channel (24) to an inlet opening for pressurized water (25) provided at the rear end (HE) of the rinsing means (20), a WLAN module (30) is arranged within the rinsing head being coupled to a camera module (11) of the imaging means (10) operatively, an antenna unit (31) of the WLAN module (30) is arranged axially behind the rinsing nozzles (21), wherein the antenna unit (31) comprises at least one antenna (32), wherein the at least one antenna (32) is arranged at least partially radially around the inlet opening for pressurized water (25), and the WLAN module (30) and the antenna unit (31) are adapted to transmit image and/or video data provided by the camera module (11) wirelessly to a control/display means (50), wherein a cover (40) is provided at the rear side of the rinsing means (20) for covering the antenna unit (31), the cover (40) comprising a plastic material and wherein the cover (40) is arranged releasably at the rear side of the rinsing means (20), wherein the lateral surface (23) of the rinsing means (20) may approximately have the shape of an hourglass, and wherein the water outlet openings (22) of the rinsing nozzles (21) are arranged in a portion (23a) of the lateral surface (23) directed backwards, wherein a cable channel (27) is formed within a wall (26) of the rinsing means (20) running from the rear side of the rinsing means (20) through the rinsing means (20) in an axial direction, wherein an electrically conducting cable is arranged within the cable channel (27) by means of which the at least one antenna (32) is coupled to the WLAN module (30), or the WLAN module (30) is coupled to the camera module (11), wherein the rinsing means (20) is formed as a monolithic body, in which the rinsing nozzles (21) are arranged, and in which the at least one water channel (24), the inlet opening for pressurized water (25), and the cable channel (27) are formed, wherein the imaging means (10) comprises a housing (12), in the interior of which an accommodation space (13) for accommodating the camera module (11) is provided, and wherein at the front end of the rinsing means (20), the cable channel (27) leads into the accommodation space (13) of the housing (12).

2. The rinsing head of claim 1, wherein the at least one antenna (32) is arranged at the rear side of the rinsing means (20).

3. The rinsing head of claim 1, wherein the WLAN module (30) is arranged axially behind the rinsing nozzles (21) or within the imaging means (10).

4. The rinsing head of claim 1, wherein the housing (12) is arranged at the rinsing means (20) releasably, and/or wherein the housing (12) comprises an opening (14) at the front end arranged coaxially with respect to an optical axis of the camera module (11).

5. The rinsing head of claim 4, wherein a double glazing pane (15) comprising multiple glass planes is arranged in the opening (14), the glass panes of which being arranged spaced apart to each other, wherein the two glass panes form a substantially pressure-tight cavity.

6. The rinsing head of claim 1, wherein the housing (12) is formed double-walled, and wherein the two walls of the housing form a substantially pressure-tight cavity.

7. The rinsing head of claim 1, wherein an energy storage, in particular, an accumulator (16) is arranged within the rinsing head for supplying the WLAN module (30) and the camera module (11) with electrical energy.

8. The rinsing head of claim 7, wherein a secondary coil means of an inductive charging system is arranged within the rinsing head for inductively charging the energy storage (16).

9. The rinsing head of claim 1, wherein a storage means (17) is arranged within the rinsing head being coupled to the camera module (11) operatively for storing image and/or video data provided by the camera module.

10. The rinsing head of claim 1, wherein a pressure sensor is assigned to the water channel (24) for monitoring the water pressure applied to the rinsing means (20), wherein the pressure data can be transmitted via the WLAN module (30) to the control/display means (50).

11. The rinsing head of claim 1, wherein the WLAN module (30) is adapted to receive control data from the control/display means (50), wherein the control data comprises data for controlling the camera module (11) and/or data for controlling the rinsing nozzles (21).

12. A sewer and/or pipe inspection system, comprising a control/display means (50) and a rinsing head (1) according to claim 1, wherein the image and/or video data provided by the camera module (11) of the rinsing head (1) can be transmitted wirelessly via the WLAN module (30) of the rinsing head (1) to the control/display means (50).

* * * * *